United States Patent
Brown et al.

(10) Patent No.: US 8,272,070 B2
(45) Date of Patent: Sep. 25, 2012

(54) CONICAL FACE SHIELD

(75) Inventors: Jonathan I. Brown, Portland, OR (US); Alan W. Reichow, Forest Grove, OR (US); Karl Citek, Forest Grove, OR (US)

(73) Assignee: Nike, Inc., Beaverton, OR (US)

( * ) Notice: Subject to any disclaimer, the term of this patent is extended or adjusted under 35 U.S.C. 154(b) by 1013 days.

(21) Appl. No.: 11/942,543

(22) Filed: Nov. 19, 2007

(65) Prior Publication Data

US 2009/0126063 A1 May 21, 2009

(51) Int. Cl.
*A61F 9/04* (2006.01)

(52) U.S. Cl. .................. 2/15; 2/6.3; 2/6.7; 2/9; 2/424

(58) Field of Classification Search .............. 2/455, 410, 2/6.3, 6.7, 424, 425, 15, 9
See application file for complete search history.

(56) References Cited

U.S. PATENT DOCUMENTS

| | | | | |
|---|---|---|---|---|
| 4,024,587 A | * | 5/1977 | Barford | 2/424 |
| D288,980 S | * | 3/1987 | Pernicka | D29/110 |
| 5,084,918 A | * | 2/1992 | Breining et al. | 2/424 |
| 5,287,562 A | * | 2/1994 | Rush, III | 2/413 |
| 5,412,814 A | * | 5/1995 | Pernicka et al. | 2/424 |
| D360,488 S | * | 7/1995 | Cardinal | D29/111 |
| 5,774,201 A | * | 6/1998 | Tackles | 351/159 |
| 5,815,848 A | | 10/1998 | Jarvis | |
| 5,953,760 A | * | 9/1999 | Powell | 2/424 |
| 6,010,217 A | * | 1/2000 | Houston et al. | 351/159 |
| 6,715,150 B1 | * | 4/2004 | Potin | 2/15 |
| 6,755,525 B2 | | 6/2004 | Reichow | |
| 6,893,127 B2 | | 5/2005 | Reichow | |
| 7,073,208 B2 | | 7/2006 | Penque | |

OTHER PUBLICATIONS

Reichow, et al., "Introduction to Behavioral Optometry", Sports Vision, 1993, 75 pages, Optometric Extension Program Foundation, United States.

(Continued)

*Primary Examiner* — Christopher Harmon
(74) *Attorney, Agent, or Firm* — Shook, Hardy & Bacon L.L.P.

(57) ABSTRACT

Conical face shields, sports helmets, and methods for orienting a conical face shield in a sports helmet are described. In embodiments, the conical face shield has at least two opposing arcuate edges, at least two opposing side edges, and a shield. The arcuate edges each have a first end, a second end, and an edge surface extending between the first end and the second end. Further, the edge surface of the first arcuate edge and the edge surface of the second arcuate edge include an arc segment and the arc segment of the edge surface of the first arcuate edge is part of an ellipse with a greater semi-minor axis than the semi-minor axis of the ellipse forming the arc segment of the edge surface of the second arcuate edge. In various other embodiments, the conical face shield may be horizontally and/or vertically tapered.

8 Claims, 7 Drawing Sheets

OTHER PUBLICATIONS

Ferreira, "An Overview of Research in Sports Vision: its History and an Optometric Perspective", The South African Optometrist, Dec. 2003, pp. 142-149, vol. 62, No. 4, Auckland Park, South Africa.

Coffey, et al., "Visual Performance Enhancement in Sports Optometry", Sports Vision 1995, pp. 158-177, Butterworth-Heinermann, United States.

Cardall, "Contact Lenses in Sport: a General Overview", Optician, Jan. 13, 2006, pp. 22-25, vol. 231, No. 6034, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

Office Action issued in U.S. Appl. No. 12/913,938 mailed on May 9, 2011, 11 pages.

* cited by examiner

CONICAL FACE SHIELD

BACKGROUND

Safety of players is of the utmost importance in any active sport, and in recent years a number of improvements have advanced the state of the protective sportswear art significantly. Particularly important to any protective sportswear scheme is a combination of headwear and eyewear to protect against injuries to a player's head and eyes. The improvements mentioned above have provided a variety of functional advantages, such as better protecting against concussions, paralysis, blindness, and UV rays, among other things.

As certain types of safety equipment change to offer improved protection to players, other types of equipment used in conjunction with the changed equipment may be impacted. For example, a combination of old and new elements may provide less-than-ideal protection. Furthermore, a change in a certain type of equipment may provide an opportunity for innovation in the design of other equipment to provide even higher levels of both protection and functionality. For instance, in a traditional football helmet/face shield combination, the face shield is a cylindrical shape with a bottom arcuate length equal to a top arcuate length. When coupled with advanced football helmets, however, the traditional cylindrical structure is awkward. For example, the cylindrical shield must be bent in order to fit into the structure of the advanced helmets. Bending the shield compromises both the safety and optical properties of the shield. Gaps occur between the shield and the helmet in which players may get fingers or clothing stuck, which can pose a grave injury risk to all involved. A poor fitting shield also raises the possibility of injuring the eyes of the wearer of the shield. Further, the distorted optical properties caused by bending the shield can prevent the player from seeing clearly, negatively impacting the quality of the players' performance.

Thus, it would be desirable to manufacture an advanced face shield designed to effectively couple with advanced sports helmets.

SUMMARY

Embodiments of the present invention provide conical face shields, sports helmets, and methods for orienting a conical face shield in a sports helmet. In various embodiments, a conical face shield may have at least two opposing arcuate edges and at least two opposing side edges, with the shield extending between those edges. Both a first and a second arcuate edge may have a first end, a second end, and an edge surface extending between the first and the second end, as well as an arc segment. In these embodiments, the arc segment of the edge surface of the first arcuate edge has an arc length greater than that of the arc segment of the edge surface of the second arcuate edge, resulting in a shield shaped similarly to the surface part of a cone. In embodiments of the present invention, the shield may be horizontally and/or vertically tapered such that the shield thickness at the shield edges is less than the shield thickness at one or more points intermediate the shield edges.

Embodiments of the present invention may further comprise attachment tabs extending from the face of the shield at an angle inclined to permit the tabs to fit securely against the surface of the sports helmet. The use of such tabs can reduce the risk of extremities or clothing getting stuck between the tab and the sports helmet. The use of such tabs can also reduce the bending and flexing experienced by a shield, both due to collisions during play and due to forces applied to the shield at attachment points.

Embodiments of the present invention may further comprise clips with angled shield contact faces. Angled, rather than perpendicular, shield contact faces on clips used to attach a shield to a face mask also prevents gaps between the shield and the clip/face mask, as well as preventing bending and flexing of the face mask.

It should be noted that this Summary is provided to generally introduce the reader to one or more select concepts described below in the Detailed Description in a simplified form. This Summary is not intended to identify key and/or required features of the claimed subject matter, nor is it intended to be used as an aid in determining the scope of the claimed subject matter.

BRIEF DESCRIPTION OF THE DRAWINGS

These and other objectives and advantages of the present invention will be more readily apparent from the following detailed description of the drawings of the preferred embodiment of the invention that are herein incorporated by reference and in which.

DETAILED DESCRIPTION

The subject matter of the present invention is described with specificity herein to meet statutory requirements. The description itself, however, is not intended to limit the scope of this patent. Rather, the inventors have contemplated that the claimed subject matter might also be embodied in other ways, to include different aspects as well as other steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide conical face shields for use with a sports helmet, sports helmets, attachment clips for attaching a face shield to a sports helmet, attachment tabs for use in securing a face shield to a sports helmet, combinations of these elements, and methods for orienting a conical face shield in a sports helmet. In various embodiments, a conical face shield may have at least two opposing arcuate edges and at least two opposing side edges with the shield extending between the edges. Both a first and a second arcuate edge have a first end, a second end, and an edge surface extending between the first and the second end, as well as an arc segment. In these embodiments, the arc segment of the edge surface of the first arcuate edge is part of a ellipse with a semi-minor axis greater than the semi-minor axis of the ellipse forming the arc segment of the edge surface of the second arcuate edge. While embodiments discussed herein refer to sports helmets with a face mask (e.g., a football helmet), it will be understood by one of ordinary skill in the art that embodiments are not limited a particular style of helmet. For example, other embodiments may include hockey helmets, ski helmets, and other various styles of helmets.

Accordingly, in one aspect, the present invention is directed to a conical face shield for orienting in a sports helmet. The conical face shield includes at least two opposing arcuate edges, the first arcuate edge oriented in a generally horizontal two-dimensional plane and the second arcuate edge oriented in another generally horizontal two-dimensional plane. The generally horizontal two-dimensional planes may or may not be parallel in various embodiments of the present invention. Each arcuate edge may have a first end, a second end, and an edge surface extending between the first end and the second end. At least two opposing side edges may be included in the conical face shield. The first side edge is oriented in a generally vertical two-dimensional plane and the second side edge is oriented in another generally vertical two-dimensional plane. The generally vertical two-dimensional planes may or may not be parallel in various embodiments of the present invention. Each side edge may have a first end, a second end, and an edge surface extending between the first end and the second end. Additionally, the conical face shield extends between the edges and may have a first shield surface and a second shield surface in a generally vertical orientation extending between the first arcuate edge and the second arcuate edge, and extending arcuately between the first side edge and the second side edge, the shield having a shield thickness defined by the distance between the first shield surface and the second shield surface. In various embodiments, without limitation, the conical face shield may be horizontally and/or vertically tapered such that the shield thickness at the side edges and the arcuate edges is less than the shield thickness at one or more points intermediate the side edges and/or the arcuate edges. For example, in various embodiments, without limitation, the shield thickness is tapered according to a critical zone for vision. The critical zone for vision includes two taper axes, each taper axis aligned with a line of sight in front of each eye. Thus, the conical face shield may be horizontally tapered such that the thickest portions of the face shield align with each line of sight, the conical face shield tapering in thickness toward the side edges and toward a central axis. Further, in various embodiments, the edge surface of the first arcuate edge and the edge surface of the second arcuate edge may include an arc segment and the arc segment of the edge surface of the first arcuate edge is part of an ellipse with a greater semi-minor axis than the semi-minor axis of the ellipse forming the arc segment of the edge surface of the second arcuate edge. Stated differently, the arc segment of the edge surface of the first arcuate edge may have an arc length greater than that of the arc segment of the edge surface of the second arcuate edge.

In another aspect, the present invention is directed to a sports helmet coupled with a conical face shield. The sports helmet is configured to maintain the conical face shield in a wearer's line of vision and includes at least two opposing arcuate edges oriented in a generally horizontal two-dimensional plane, each edge having a first end, a second end, and an edge surface extending between the first end and the second end, and at least two opposing side edges oriented in a generally vertical two-dimensional plane, each edge having a first end, a second end, and an edge surface extending between the first end and the second end. The sports helmet further includes a shield having a first shield surface and a second shield surface in a generally vertical orientation extending between the first arcuate edge and the second arcuate edge, and extending arcuately between the first side edge and the second side edge, the shield having a shield thickness defined by the distance between the first shield surface and the second shield surface. In this aspect, the edge surface of the first arcuate edge and the edge surface of the second arcuate edge include an arc segment and the arc segment of the edge surface of the first arcuate edge is part of an ellipse with a greater semi-minor axis than the semi-minor axis of the ellipse forming the arc segment of the edge surface of the second arcuate edge. Stated differently, the arc segment of the edge surface of the first arcuate edge has an arc length greater than that of the arc segment of the edge surface of the second arcuate edge. Again, in various embodiments, without limitation, the conical face shield may be horizontally and/or vertically tapered such that the shield thickness at the side edges and the arcuate edges is less than the shield thickness at one or more points intermediate the side edges and/or the arcuate edges. For example and as discussed above, in various embodiments, without limitation, the shield thickness is tapered according to a critical zone for vision. The critical zone for vision includes two taper axes, each taper axis aligned with a line of sight in front of each eye. Thus, the conical face shield may be horizontally tapered such that the thickest portions of the face shield align with each line of sight, the conical face shield tapering in thickness toward the side edges and toward a central axis.

In another embodiment, the present invention is directed to a method for orienting a conical face shield in a sports helmet for maintaining the conical face shield in a wearer's field of vision. The method includes providing a sports helmet configured to maintain the conical face shield in the wearer's field of vision, and providing a shield having a first shield surface and a second shield surface in a generally vertical orientation extending between a first arcuate edge and a second arcuate edge, and extending arcuately between a first side edge and a second side edge, the shield having a shield thickness defined by the distance between the first shield surface and the second shield surface. The method further includes mounting the shield to the support. In this aspect, the edge surface of the first arcuate edge and the edge surface of the second arcuate edge include an arc segment and the arc segment of the edge surface of the first arcuate edge is part of an ellipse with a greater semi-minor axis than the semi-minor axis of the ellipse forming the arc segment of the edge surface of the second arcuate edge. Stated differently, the arc segment of the edge surface of the first arcuate edge has an arc length greater than that of the arc segment of the edge surface of the second arcuate edge.

In another embodiment, the present invention is directed to one or more attachment clips. The attachment clips may include a face mask coupling portion, an outer shield contact face extending angularly and non-perpendicularly from the coupling portion, and an inner shield contact face extending from the coupling portion at a predetermined distance from the outer shield contact face. The outer shield contact face may be angled at an acute angle relative to the coupling portion, rather than perpendicular, allowing the clip to secure the face shield to the face mask while preventing gaps between the clip and the face shield and preventing bending and flexing of the face shield. The inner shield contact face, if present, may extend substantially parallel to the outer shield contact face. The predetermined distance between the outer shield contact face and the inner shield contact face may be selected to fit the width of the particular shield being used.

In yet another embodiment, the present invention is directed to one or more attachment tabs extending from the face shield at an angle inclined to permit the tabs to be positioned securely and substantially flush against the surface of the sports helmet. The one or more coupling tabs may include at least two opposing side edges oriented generally vertically, a top edge oriented generally horizontally, and a face shield coupling edge where the attachment tab is coupled to the face shield. In this aspect, the face shield coupling edge is oriented at an angle so that the attachment tab may extend from the face shield angularly, allowing the tab to be securely positioned against the surface of the sports helmet. Consequently, tab extends in plane different from any plane including both a point on the upper arcuate edge of the face shield and a point on the lower arcuate edge of the face shield.

Having briefly described an overview of embodiments of the present invention, an exemplary conical face shield environment is described below. One skilled in the art will appreciate that the conical shield, the attachment clips, and the attachment clips may be used independently or in conjunction with one another.

Figure 1:
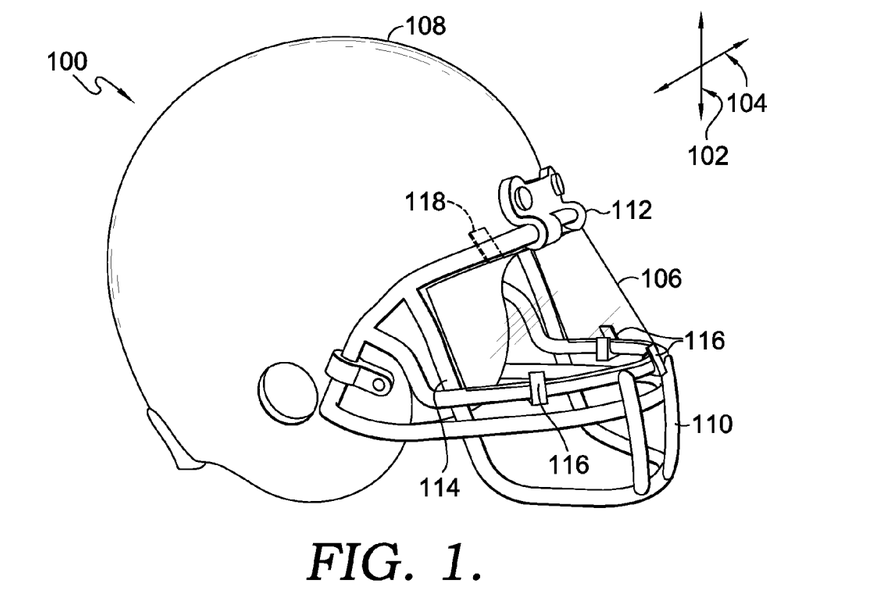
FIG. 1 is a profile view of a sports helmet coupled with a conical face shield, in accordance with an embodiment of the present invention.
Figure 2:
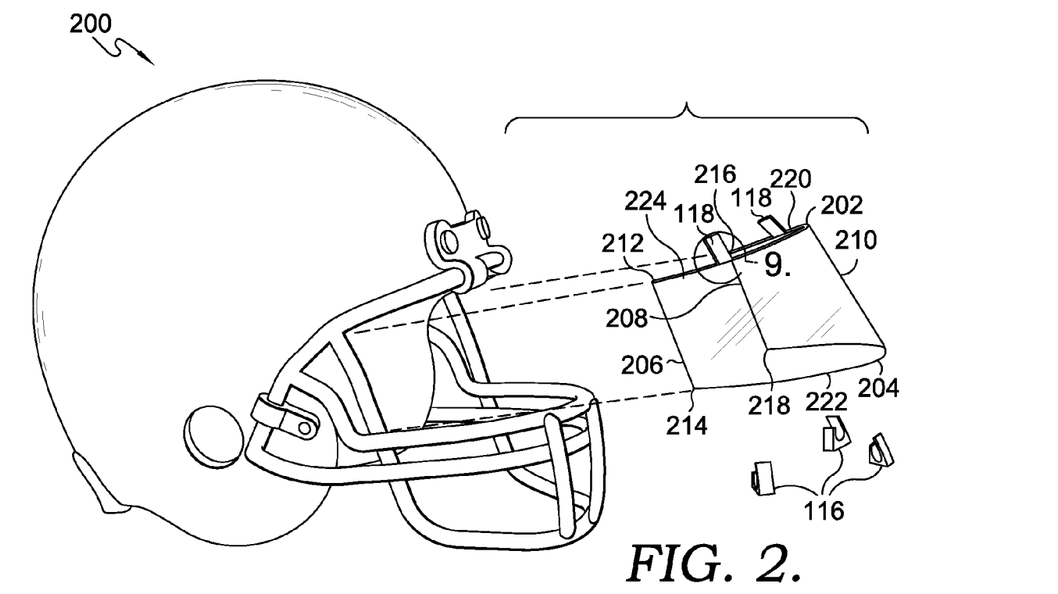
FIG. 2 is a profile view of a sports helmet with a conical face shield removed, illustrating the conical face shield in more detail, in accordance with an embodiment of the present invention.

Referring to the drawing figures in general, and initially to FIGS. 1-2 in particular, an exemplary environment for implementing embodiments of the present invention is shown and designated generally as reference numeral 100. Throughout this specification, the term conical face shield is intended to include various styles of transparent face shields, including face shields composed of various materials and face shields having various colors and various degrees of shading. Face shield composition, color, and shading will be well known to one of ordinary skill in the art and will not be further discussed herein. As used herein, the terms "vertical" and "horizontal" and variations thereof define positions of various components of the conical face shield, "vertical" being the direction of vertical axis 102 and "horizontal" being the direction of horizontal axis 104, as illustrated.

Referring now to FIGS. 1-2, the conical face shield 106 will be discussed. FIG. 1 illustrates conical face shield 106 oriented within a sports helmet 108, while FIG. 2 illustrates conical face shield 106 removed from sports helmet 108 for illustrative purposes at 200. As can be appreciated with reference to FIG. 2, conical face shield 106 includes an upper arcuate edge 202, a lower arcuate edge 204, two side edges 206 and 208, and a shield portion 210. Upper arcuate edge 202 and lower arcuate edge 204 are each oriented in a separate generally horizontal two-dimensional plane, as depicted in FIG. 2, and include first ends 212 and 214, and second ends 216 and 218. The two generally horizontal two-dimensional planes may or may not be parallel in various embodiments of the present invention. As illustrated in FIGS. 1-2, upper arcuate edge 202 and lower arcuate edge 204 each include an arc segment (as illustrated by upper arc segment 220 and lower arc segment 222). As illustrated here, in various embodiments, the entirety of the upper arcuate edge 202 and lower arcuate edge 204 includes arc segments 220 and 222. In various other embodiments, the arc segments 220 and 222 may make up only a portion of upper arcuate edge 202 and lower arcuate edge 204. Various configurations are contemplated and within the scope of the present invention. For example, either one or both of upper arcuate edge 202 and lower arcuate edge 204 may include a portion that is substantially linear.

Side edges 206 and 208 share common ends with arcuate edges 202 and 204. Thus, side edge 206 extends from first end 212 of upper arcuate edge 202 to first end 214 of lower arcuate edge 204. Similarly, side edge 208 extends from second end 216 of upper arcuate edge 202 to second end 218 of lower arcuate edge 204. Shield portion 210 extends in a generally vertical orientation between lower arcuate edge 204 and upper arcuate edge 202 and extends in an arcuate orientation between side edges 206 and 208. Shield portion 210 includes an inner shield surface (not shown) and an outer shield surface (not shown) and has a shield thickness 224 defined by the distance between the inner shield surface and the outer shield surface. Various embodiments involving shield surfaces and thicknesses will be discussed in more detail herein with reference to various other depictions of the conical face shield.

As illustrated in FIG. 1, conical face shield 106 is oriented within a sports helmet 108 and bounded by a face mask 110, a helmet forward section 112, and a side bar 114. In various embodiments, conical face shield 106 is held into place within a sports helmet 108 with one or more conical shield attachment clips 116 and one or more conical shield attachment tabs 118. Specific details of the configuration of conical shield attachment clips 116 and conical shield attachment tabs 118 will be further discussed herein. Embodiments of the present invention, however, are not limited to any particular configuration for orientation within a sports helmet. For example, without limitation, where the sports helmet is a hockey helmet, face mask 110 may not be present and conical face shield 106 may not be bounded, either on the sides, or on the bottom, by face mask 110. Further, embodiments of the present invention are not limited to any particular attachment mechanism such as conical shield attachment tab 118. For example, without limitation, conical face shield 106 may be coupled, at its uppermost portion, to sports helmet 108 using bolts, screws, rivets, or various other means. When conical face shield 106 is coupled with sports helmet 108, conical face shield 106 is substantially flush with sports helmet 108

(despite the configuration of sports helmet 108) such that no significant gaps occur between conical face shield 106 and sports helmet 108.

As will be appreciated by one of ordinary skill in the art with reference to FIGS. 1-2, lower arc segment 222 of lower arcuate edge 204 has an arc length longer than upper arc segment 220 of upper arcuate edge 202. Stated differently, where the shape of upper arc segment 220 and lower arc segment 222 are defined by an elliptical arc, the semi-minor axis of the ellipse with a portion creating lower arc segment 222 is greater than the semi-minor axis of the ellipse with a portion creating upper arc segment 220. Thus, in various embodiments of the present invention, the conical face shield can be considered a portion of a cone. Embodiments of the present invention, however, are not limited to circular arc configurations. For example, without limitation, upper arc segment 220 and lower arc segment 222 can be elliptical arcs. The conical configuration of the present invention can be further appreciated with reference to FIG. 3.

Figure 3:
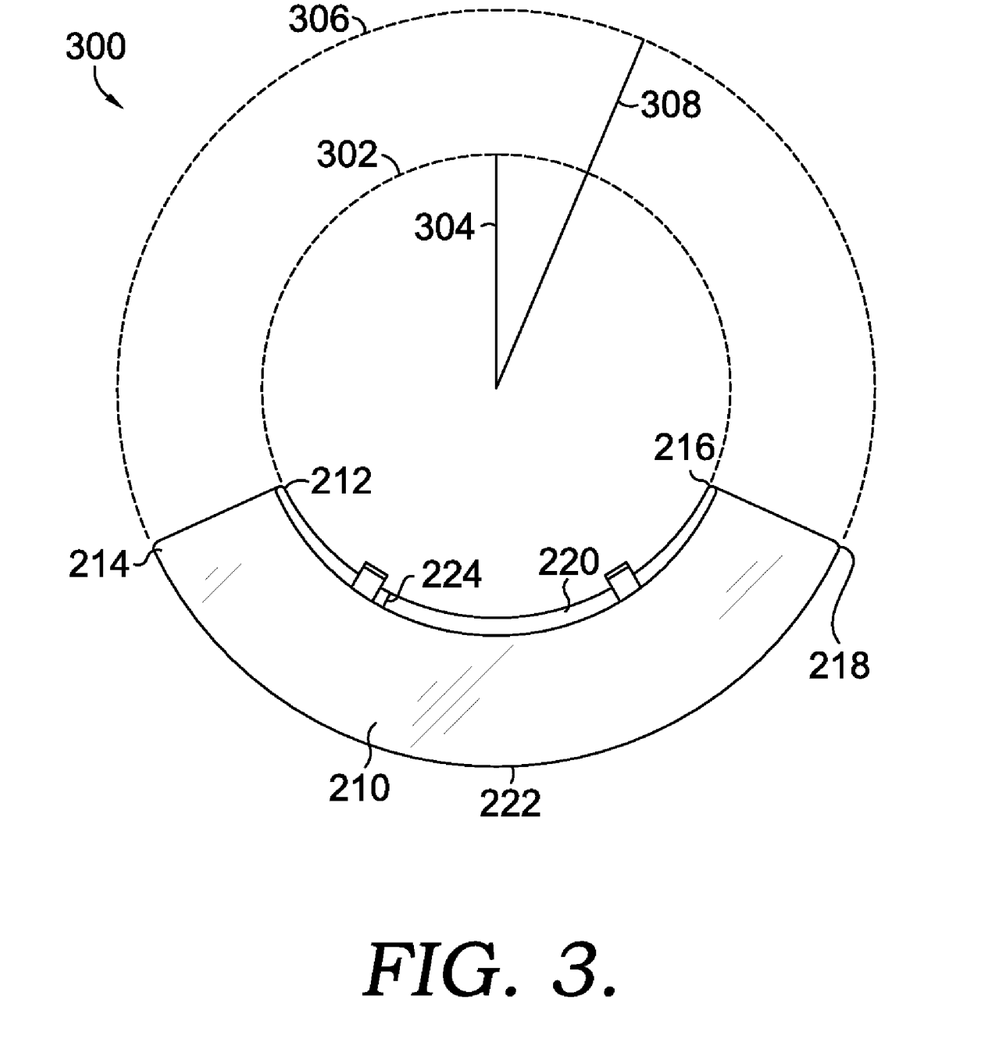
FIG. 3 is a vertical view of a conical face shield, in accordance with an embodiment of the present invention.

Turning now to FIG. 3, a vertical view of a conical face shield, in accordance with an embodiment of the present invention, is illustrated and designated generally as reference numeral 300. As previously described, lower arc segment 222 of lower arcuate edge 204 may have an arc length greater than upper arc segment 220 of upper arcuate edge 202. In various embodiments, upper arc segment 220 may be elliptical and, for exemplary purposes, may be considered part of upper ellipse 302 having semi-minor axis 304. Further, lower arc segment 222 can be elliptical and, for exemplary purposes, may be considered part of lower ellipse 306 having semi-minor axis 308. Semi-minor axis 304 of upper ellipse 302 is less than semi-minor axis 308 of lower ellipse 306. The elliptical configuration discussed herein is for exemplary purposes only and is not meant to limit the scope of the present invention to a particular arc type. Further, the elliptical configuration may include circular configurations. For example, as illustrated in FIG. 3, upper ellipse 302 and lower ellipse 306 may be circular, in which case the arc segments 220 and 222 will be circular arcs. In the circular arc example, semi-minor axis 304 and semi-minor axis 308 may be considered radii.

Figure 4:
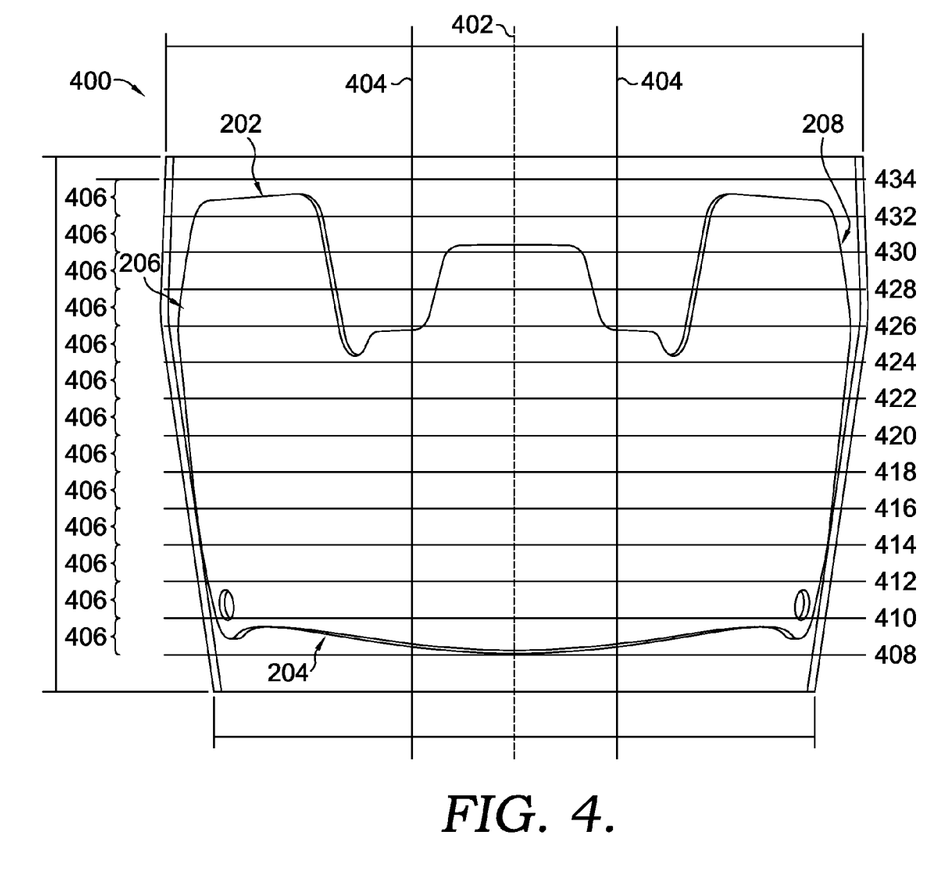
FIG. 4 is a perspective view of a conical face shield, illustrating taper axes and exemplary dimensions, in accordance with an embodiment of the present invention.

Turning now to FIG. 4, a perspective view of a conical face shield, illustrating taper axes and exemplary dimensions, in accordance with an embodiment of the present invention, is illustrated and designated generally as reference numeral 400. As can be appreciated with reference to FIG. 4, the conical face shield may include a first and a second taper axis 404 oriented on each side of a vertical central axis 402. In various embodiments of the present invention, the taper axes 404 may be the point at which the horizontal taper of the conical shield begins. Stated differently, in various embodiments, without limitation, the taper axes 404 may have a constant thickness. For instance, in various embodiments, the taper axes 404 may be the thickest portion of the conical face shield. As will be understood and appreciated by one of ordinary skill in the art, the conical face shield may taper from the taper axes 404 to a thinner portion at side edge 206 and side edge 208. The conical face shield may also, in various embodiments, taper between the taper axes 404 to a thinner portion at vertical central axis 402. Thus, as will be understood and appreciated by one of ordinary skill in the art, in various embodiments of the present invention, the horizontal taper does not merely taper from a center region toward each edge, but rather tapers from two taper axes 404 going both toward side edges 206 and 208, as well as toward vertical central axis 402. In various embodiments of the present invention, without limitation, the taper axes 404 are aligned with a user's eyes such that the thickest portion of the conical face shield will be in front of the eyes of the conical shield user. As will be understood and appreciated by one of ordinary skill in the art, in various embodiments the horizontal taper from the taper axes 404 will be combined with a vertical taper. In various embodiments, the thickest portion of the vertical taper may also be in the critical zone for vision.

In various embodiments, without limitation, upper arcuate edge 202 may have a arcuate length greater than that of lower arcuate edge 204. By way of example, without limitation, where the conical face shield is divided into 10 mm segments, as indicated by segment 406, the edge arcuate length associated with each reference numeral 408-434 may be:

| Reference Numeral | Position from Bottom Edge | Edge Arcuate Length |
|---|---|---|
| 408 | 10 mm | 168.2 mm |
| 410 | 20 mm | 171.3 mm |
| 412 | 30 mm | 174.3 mm |
| 414 | 40 mm | 177.3 mm |
| 416 | 50 mm | 180.2 mm |
| 418 | 60 mm | 183.0 mm |
| 420 | 70 mm | 185.8 mm |
| 422 | 80 mm | 188.5 mm |
| 424 | 90 mm | 191.2 mm |
| 426 | 100 mm | 193.7 mm |
| 428 | 110 mm | 194.2 mm |
| 430 | 120 mm | 193.6 mm |
| 432 | 130 mm | 192.8 mm |
| 434 | 140 mm | 191.9 mm |

These dimensions are intended for exemplary purposes only and are in no way intended to limit the scope of the present invention to any particular configuration. Rather, the dimensions are intended to illustrate to those of ordinary skill in the art an exemplary conical face shield configuration within one of the various embodiments of the present invention. As will be understood and appreciated by one of ordinary skill in the art, the increase in arcuate length per 10 mm section may or may not be linear in various embodiments of the present invention. Also, as will be understood with reference to FIG. 4, there may be a shield bend (here it occurs at section 428), wherein the arcuate edge length begins to decrease. Stated differently, upper arcuate edge 202, in various embodiments, may or may not have the greatest arcuate length of any section.

Figure 5:
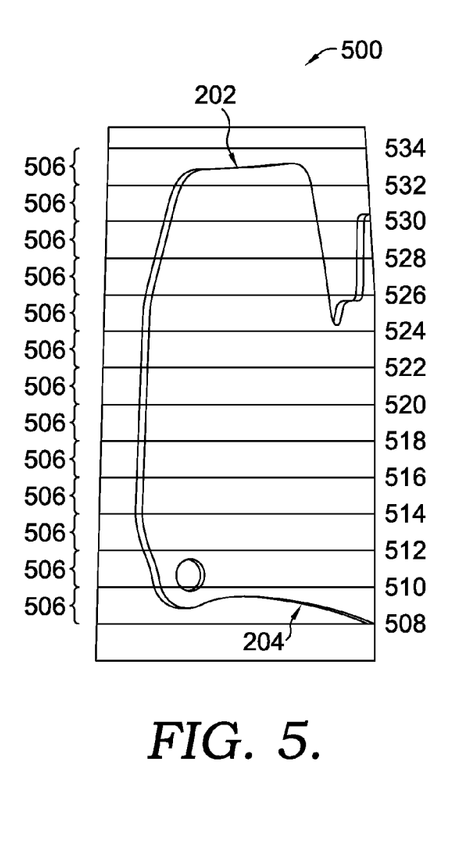
FIG. 5 is a perspective view of a portion of a conical face shield, illustrating exemplary semi-minor axes, in accordance with and embodiment of the present invention.

Turning now to FIG. 5, a perspective view of a portion of a conical face shield, illustrating exemplary semi-minor axes, in accordance with an embodiment of the present invention, is illustrated and designated generally as reference numeral 500. As previously stated with reference to FIG. 4, in various embodiments of the present invention, upper arcuate edge 202 has an arcuate edge length greater than that of lower arcuate edge 204. Stated differently, the semi-minor axis of the ellipse for upper arcuate edge 202 may be greater than the semi-minor axis of the ellipse for lower arcuate edge 204. By way of example, without limitation, where the conical face shield is divided into 10 mm segments, as indicated by segment 506, the semi-minor axis associated with each reference numeral 508-534 may be:

| Reference Numeral | Position from Bottom Edge | Semi-Minor Axis |
|---|---|---|
| 508 | 10 mm | 82.8 mm |
| 510 | 20 mm | 84.5 mm |

-continued

| Reference Numeral | Position from Bottom Edge | Semi-Minor Axis |
|---|---|---|
| 512 | 30 mm | 86.3 mm |
| 514 | 40 mm | 88.1 mm |
| 516 | 50 mm | 89.9 mm |
| 518 | 60 mm | 91.6 mm |
| 520 | 70 mm | 93.4 mm |
| 522 | 80 mm | 95.2 mm |
| 524 | 90 mm | 97.0 mm |
| 526 | 100 mm | 98.7 mm |
| 528 | 110 mm | 100.5 mm |
| 530 | 120 mm | 101.1 mm |
| 532 | 130 mm | 101.0 mm |
| 534 | 140 mm | 100.6 mm |

In addition, the radii of the semi-minor axes on the inside surface of a shield in accordance with the present invention may vary with vertical position to provide a desired refractive power along each horizontal meridian. The desired refractive power in all horizontal meridians may be zero for implementations. However, refractive powers that are either constant or vary with vertical position are possible in accordance with the present invention.

These dimensions are intended for exemplary purposes only and are in no way intended to limit the scope of the present invention to any particular configuration. Rather, the dimensions are intended to illustrate to those of ordinary skill in the art an exemplary conical face shield configuration within one of the various embodiments of the present invention. As will be understood and appreciated by one of ordinary skill in the art, the increase in semi-minor axis length in the 10 mm sections may correspond with the increase in arcuate edge length discussed previously with reference to FIG. 4. Thus, the change in semi-minor axis length may or may not be linear in various embodiments of the present invention. Also, as will be understood with reference to FIG. 4, there may be a shield bend (here it occurs at section 530), wherein the semi-minor axis length begins to decrease. Stated differently, upper arcuate edge 202, in various embodiments, may or may not have the greatest semi-minor axis length of any section.

Figure 6:
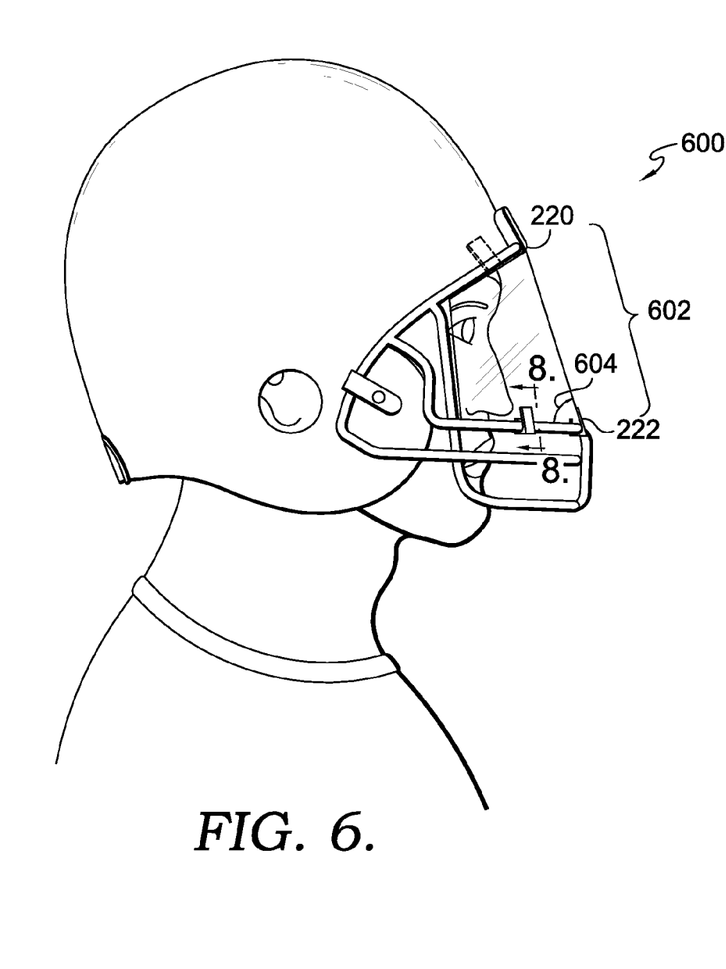
FIG. 6 is a profile view of a sports helmet coupled with a conical face shield in use by a wearer, in accordance with an embodiment of the present invention.

Turning now to FIG. 6, a profile view of a sports helmet coupled with a conical face shield in use by a wearer, in accordance with an embodiment of the present invention, is illustrated and designated generally as reference numeral 600. Profile view 600 includes, among other things, a shield profile 602 and a shield angle 604. As will be appreciated by one of ordinary skill in the art, in FIG. 6, shield profile 602 is substantially linear between lower arc segment 222 and upper arc segment 220. Shield angle 604 will vary depending upon the difference in arc length of lower arc segment 222 and upper arc segment 220 and also depending upon the mounting of conical face shield 106 within sports helmet 108. Various lengths of lower arc segment 222 and upper arc segment 220 are contemplated and within the scope of the present invention. Thus, shield angle 602 may vary according to the length of arc segments 220 and 222.

Figure 7:
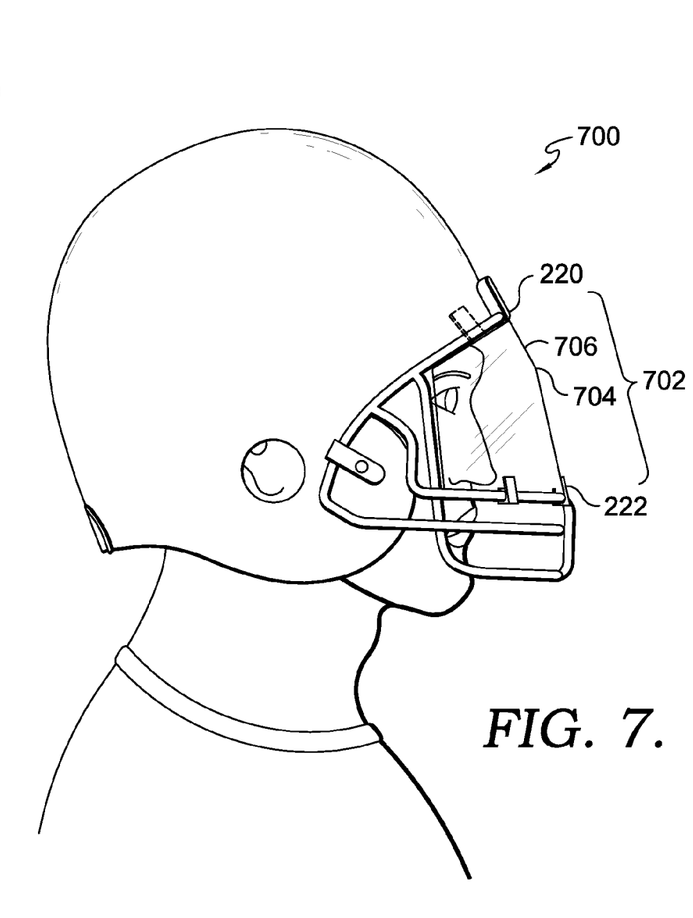
FIG. 7 is a profile view of a sports helmet coupled with a conical face shield in use by a wearer, in accordance with an embodiment of the present invention.

Turning now to FIG. 7, a profile view of a sports helmet coupled with a conical face shield in use by a wearer, in accordance with an embodiment of the present invention, is illustrated and designated generally as reference numeral 700. Profile view 700 includes a shield profile 702, a shield bend 704, and a bend angle 706. As will be appreciated by one or ordinary skill in the art, in FIG. 7, shield profile 702 includes a bend 704 and is, therefore, not substantially linear between lower arc segment 222 and upper arc segment 220.

Although the illustrated example in FIG. 7 shows shield bend 704 nearer the upper arc segment 220 than the lower arc segment 222, shield bend 704, in various embodiments, may be located at any point intermediate lower arc segment 222 and upper arc segment 220. Further, in various embodiments, there may be more than one shield bend 704. Still further, in various exemplary embodiments, shield bend 704 may be an obtuse angle in the conical face shield, conceptually creating two conical shapes—one extending between lower arc segment 222 and shield bend 704, and another extending between shield bend 704 and upper arc segment 220. In various other embodiments, shield bend 704 may be more of an arcuate shape than an obtuse angle. Each of the discussed embodiments, and variations thereof, are contemplated and within the scope of the present invention.

Figure 8:
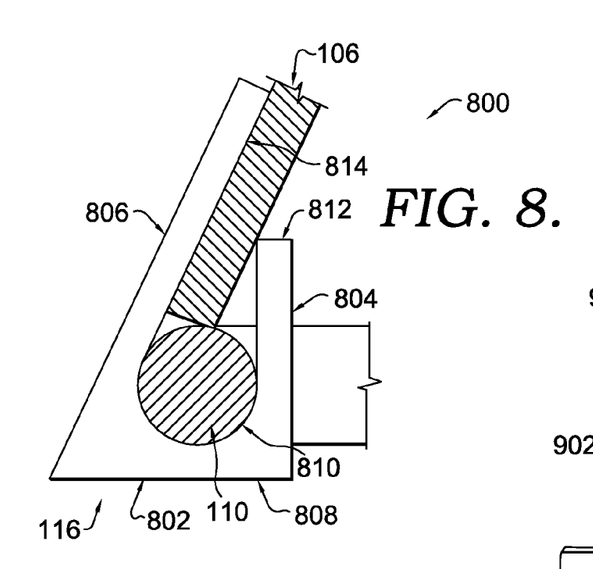
FIG. 8 is a cross-sectional view of a conical shield attachment clip, in accordance with an embodiment of the present invention.

Turning now to FIG. 8, a cross-sectional view of a conical shield attachment clip, in accordance with an embodiment of the present invention, is illustrated and designated generally as reference numeral 800. Cross-sectional view 800 includes a conical shield attachment clip 116 coupled with face mask 110 and conical face shield 106. Conical shield attachment clip 116 includes a face mask coupling portion 802, a inner shield contact face 804, and an angular outer shield contact face 806. As can be appreciated with reference to FIG. 8, face mask coupling portion 802 may include an outer surface 808 and an inner surface 810. In various embodiments, without limitation, outer surface 808 may generally planar and oriented in a generally horizontal two-dimensional plane. Inner surface 810 may be configured to be coupled with face mask 110. Thus, inner surface 810 may include various configurations to accommodate various face masks. For example, without limitation, inner surface 810 may be circular in shape, to accommodate a tubular face mask. In various embodiments, without limitation, face mask coupling portion 802 may be coupled with conical shield attachment clip 116 to face mask 110 using various attachment means. By way of example, without limitation, the coupling may be a friction fit. In various other embodiments, the coupling may use a screw, bolt, or adhesive, among other things. In various embodiments, without limitation inner shield contact face 804 may extend generally vertically from face mask coupling portion 802 and is generally perpendicular to outer surface 808 of face mask coupling portion 802. Alternatively, inner shield contact face 804 may extend substantially parallel to outer shield contact face 806. Shield positioning face 804 may include an upper edge 812 that may be in contact with conical face shield 106. Outer shield contact face 806 may extend angularly from face mask coupling portion 802 and is non-perpendicular to outer surface 808 of face mask coupling portion 802, and may form an acute angle relative to outer surface 808 of coupling portion 802. Outer shield contact face 806 may include an inner surface 814 that contacts the outer face of conical face shield 106. As can be appreciated with reference to FIG. 8, in various embodiments, the angular configuration of angular shield contact face 806 allows inner surface 814 of angular shield contact face 806 to maintain contact with conical face shield 106 without significant gaps. Thus, conical shield attachment clip 116 is configured to accommodate the conical structure of conical face shield 106.

Figure 9:
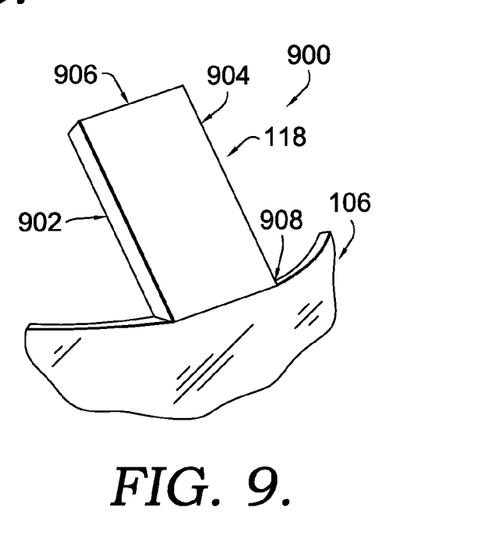
FIG. 9 is a perspective view of a conical shield attachment tab, in accordance with an embodiment of the present invention.

Turning now to FIG. 9, a perspective view of a conical shield attachment tab, in accordance with an embodiment of the present invention, is illustrated and designated generally as reference numeral 900. Perspective view 900 includes a conical shield attachment tab 118 coupled with conical face shield 106. Conical shield attachment tab 118 includes two side edges 902 and 904 oriented generally vertically, a top edge 906 oriented generally horizontally, and a face shield coupling edge 908. As can be appreciated with reference to FIG. 9, face shield coupling edge 908 of conical shield attachment tab 118 is oriented at an angle, causing conical shield attachment tab 118 to extend from conical face shield 106 angularly. Conical shield attachment tab 118 and conical face shield 106 may be coupled at face shield coupling edge 908 in any of a variety of manners. For example, without limitation, in various embodiments conical shield attachment tab 118 and face shield 106 are molded together. In these embodiments, there is no joint or attachment means necessary to couple conical shield attachment tab 118 to conical face shield 106 because conical shield attachment tab 118 is a part of conical face shield 106, extending from face shield coupling edge 908. In various other embodiments, conical shield attachment tab 118 may be coupled to conical face shield 106 using any of a variety of attachment means including adhesive. In various embodiments, conical shield attachment tab 118 extends angularly from conical face shield 106 and, thus, is configured to accommodate orientation of conical face shield 106 into a sports helmet, such as sports helmet 108 of FIG. 1.

Figure 10:
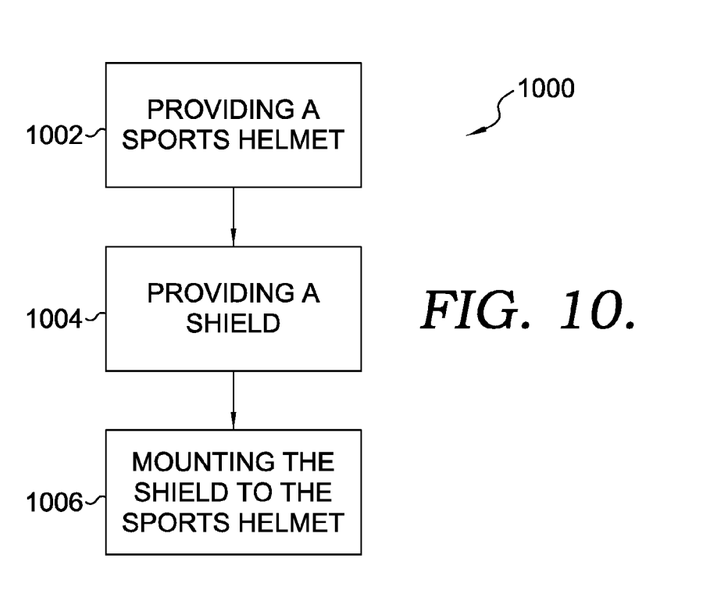
FIG. 10 is a flow diagram illustrating an exemplary method for orienting a conical face shield in a sports helmet for maintaining the conical face shield in a wearer's field of vision, in accordance with an embodiment of the present invention.

Turning now to FIG. 10, a flow diagram illustrating an exemplary method for orienting a conical face shield in a sports helmet for maintaining the conical face shield in a wearer's field of vision, in accordance with an embodiment of the present invention, is illustrated and designated generally as reference numeral 1000. Initially, as indicated at block 1002, a sports helmet is provided (e.g. a sports helmet as previously discussed with general reference to FIGS. 1-2 and FIGS. 6-7). As discussed above, in various embodiments, the sports helmet may be a football helmet with a face mask. Embodiments of the present invention, however, are not limited to a specific configuration of sports helmet. For example, without limitation, the sports helmet provided at step 1002 may be a hockey helmet, a ski helmet, or any type of other helmet that may be coupled with a conical face shield.

Next, as indicated at block 1004, a shield is provided (e.g. a shield as previously discussed with reference to FIGS. 1-2 and FIGS. 6-7). As previously stated, the shield has an upper arc segment and a lower arc segment configured so that the length of the lower arc segment is greater than the length of the upper arc segment, forming a conical configuration. As previously discussed, embodiments of the present invention are not limited to any particular shield style nor limited to specific optical functionality. For instance, without limitation, various optical properties are contemplated and within the scope of the present invention. Further, various material compositions and tinting styles are also contemplated and within the scope of this invention.

Next, as indicated at block 1006, the shield is mounted to the sports helmet (e.g. as previously discussed with reference to FIGS. 8-9 involving conical shield attachment clips and conical shield attachment tabs). As previously stated, however, embodiments of the present invention are not limited to any particular mounting formats. For example, without limitation, some sports helmets may not be configured to support conical shield attachment clips because they may lack a face mask. In another example, without limitation, some sports helmets may use devices other than conical shield attachment tabs (e.g. bolts) to couple the shield with the helmet forward section.

Figure 11:
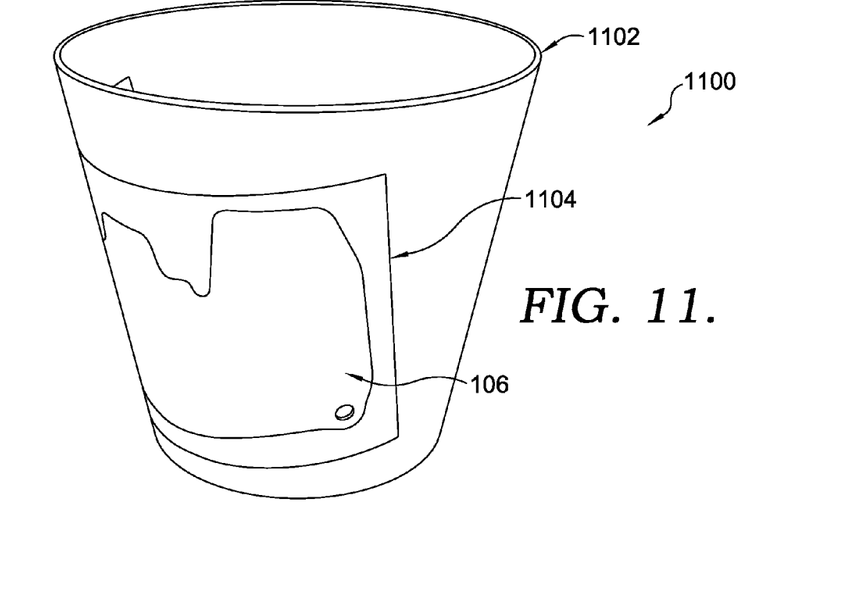
FIG. 11 is a perspective view of a conical face shield cone including a conical face shield blank and a conical face shield, in accordance with an embodiment of the present invention.
Figure 12:
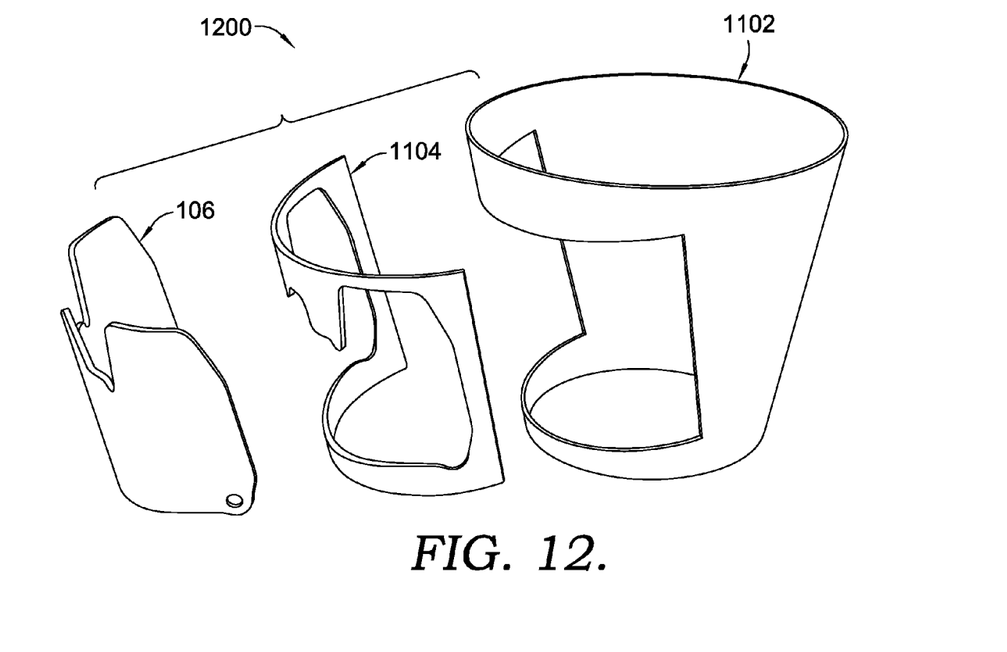
FIG. 12 is another perspective view of a conical face shield cone including a conical face shield blank and a conical face shield, the conical face shield blank and conical face shield removed from the conical face shield cone, in accordance with an embodiment of the present invention.

Turning now to FIG. 11, a perspective view of a conical face shield cone including a conical face shield blank and a conical face shield, in accordance with an embodiment of the present invention, is illustrated and designated generally as reference numeral 1100. As will be appreciated with reference to FIG. 11, the conical face shield cone 1102 may be a cone-shaped mold for creating a conical face shield. More particularly, the conical face shield cone 1102 includes a conical face shield blank 1104 and a conical face shield 106. As will be understood and appreciated by one of ordinary skill in the art, the cone structure of conical face shield cone 1102 may be used as a mold to form conical face shield 106. For example, in FIG. 12, another perspective view of a conical face shield cone including a conical face shield blank and a conical face shield, the conical face shield blank and conical face shield removed from the conical face shield cone, in accordance with an embodiment of the present invention, is illustrated and designated generally as reference numeral 1200. In the perspective view of FIG. 12, conical face shield blank 1104 has been removed from conical face shield cone 1102, and conical face shield 106 has been formed out of conical face shield blank 1104.

Figure 13:
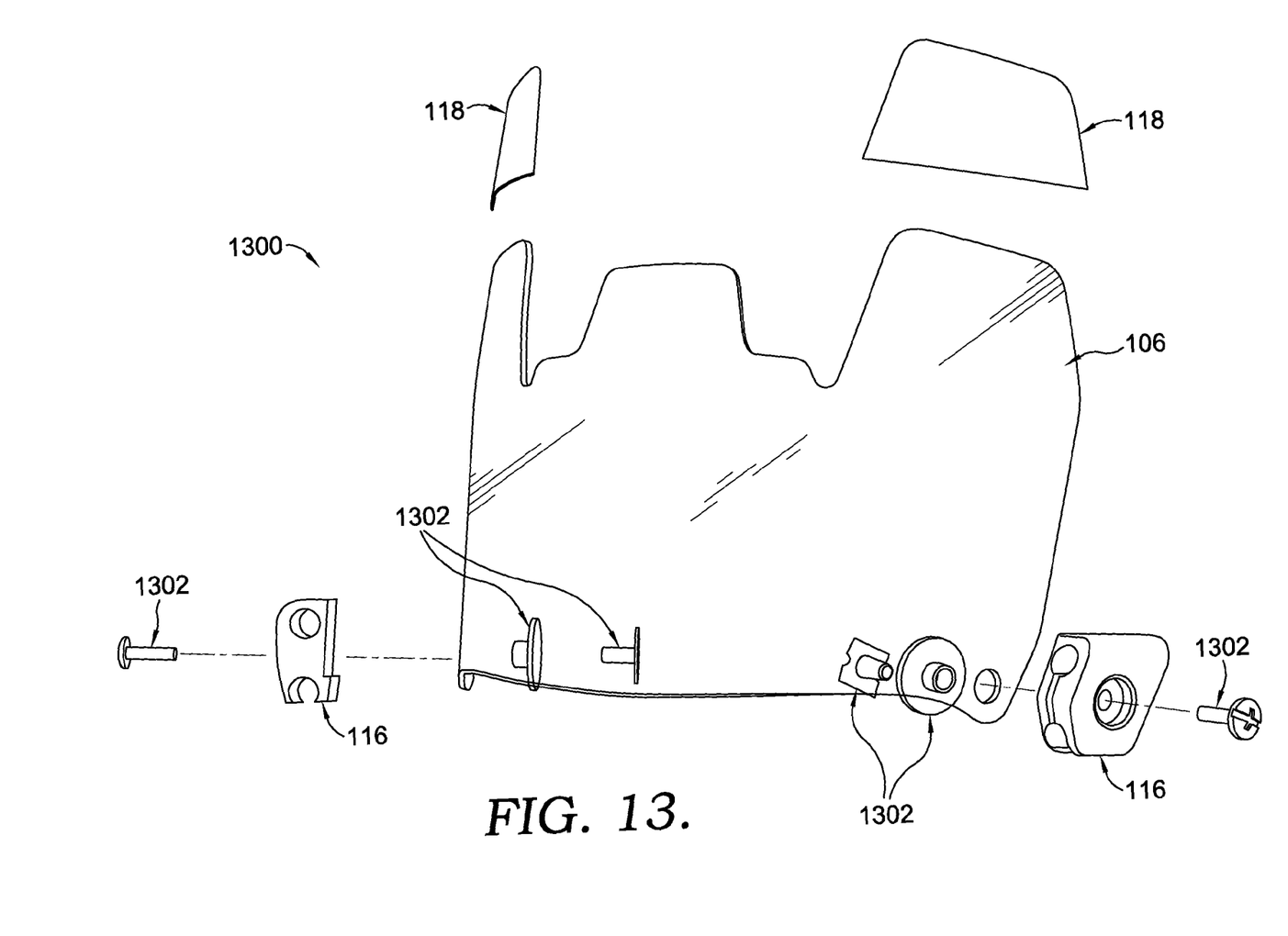
FIG. 13 is a perspective view of a conical face shield, including conical shield attachment clips and conical shield attachment tabs, in accordance with an embodiment of the present invention.

Turning now to FIG. 13, a perspective view of a conical face shield, including conical shield attachment clips and conical shield attachment tabs, in accordance with an embodiment of the present invention, is illustrated and designated generally as reference numeral 1300. As illustrated, FIG. 13 presents a perspective view of various embodiments of the present invention. Perspective view 1300 includes conical face shield 106, conical shield attachment clips 116, and conical shield attachment tabs 118. Further, fastening mechanisms 1302 are illustrated as coupling conical shield attachment clips 116 to conical face shield 106. As will be understood and appreciated by one of ordinary skill in the art, embodiments of the present invention are not limited to any particular fastening mechanisms 1302. Instead, various mechanism may be used to couple conical face shield 106 and conical shield attachment clips 116. For example, without limitation, in various embodiments conical face shield 106 may be coupled with conical shield attachment clips 116 with an adhesive.

One skilled in the art will appreciate that the conical face shield, angled attachment tabs, and angled attachment clips may be used together, but will further realize that they may be used independently and in various combinations. For example, a conical face shield need not utilize angled attachment tabs and/or angled attachment clips. By way of further example, a non-conical face shield may benefit from the use of angled attachment tabs and/or angled attachment clips.

In each of the exemplary methods described herein, various combinations and permutations of the described blocks or steps may be present and additional steps may be added. Further, one or more of the described blocks or steps may be absent from various embodiments. It is contemplated and within the scope of the present invention that the combinations and permutations of the described exemplary methods, as well as any additional or absent steps, may occur. The various methods are herein described for exemplary purposes only and are in no way intended to limit the scope of the present invention.

The present invention has been described herein in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain the ends and objects set forth above, together with other advantages which are obvious and inherent to the methods, conical face shields, and sports helmets. It will be understood that certain features and sub-combinations are of utility and may be employed without reference to other features and sub-combinations. This is contemplated by and within the scope of the claims.

The invention claimed is:

1. A conical face shield for attachment to a sports helmet, comprising:
   a first arcuate edge oriented in a first generally horizontal two-dimensional plane, the first arcuate edge having a first end, a second end, and an edge surface extending between the first end and the second end;
   a second arcuate edge oriented in a generally horizontal two-dimensional plane, the second arcuate edge having a first end, a second end, and an edge surface extending between the first end and the second end; wherein the first generally horizontal two-dimensional plane and the second generally horizontal two-dimensional plane are separate two-dimensional planes;
   a first side edge oriented in a two-dimensional plane connecting the first end of the first arcuate edge and the first end of the second arcuate edge, the first side edge having a first end, a second end, and a first edge surface extending between the first end and the second end, the first edge surface comprised of a first linear segment extending along a portion of the first edge surface;
   a second side edge oriented in a two-dimensional plane connecting the second end of the first arcuate edge and the second end of the second arcuate edge, the second side edge having a first end, a second end, and a second edge surface extending between the first end and the second end, the second edge surface comprised of a second linear segment extending along a portion of the second edge surface; and
   a conically-shaped shield extending between the first arcuate edge and the second arcuate edge and extending arcuately between the first side edge and the second side edge, the conically-shaped shield having a shield thickness, the conically-shaped shield comprised of a surface portion that extends arcuately from the first linear segment of the first edge surface to the second linear segment of the second edge surface,
   wherein the edge surface of the first arcuate edge includes a first arc segment and the edge surface of the second arcuate edge includes a second arc segment,
   wherein the arc segment of the edge surface of the first arcuate edge is part of a first ellipse,
   wherein the arc segment of the edge surface of the second arcuate edge is part of a second ellipse, and
   wherein the semi-minor axis of the first ellipse is greater than the semi-minor axis of the second ellipse.

2. The conical face shield of claim 1, wherein the shield thickness is horizontally tapered such that the shield thickness at each of the first side edge and the second side edge is less than the shield thickness at a point intermediate the first side edge and the second side edge.

3. The conical face shield of claim 2, wherein the shield thickness is vertically tapered such that the shield thickness at each of the first arcuate edge and the second arcuate edge is less than the shield thickness at a point intermediate the first arcuate edge and the second arcuate edge.

4. The conical face shield of claim 1, further comprising:
   a vertical central axis located intermediate the first side edge and the second side edge;
   a first vertical taper axis located intermediate the vertical central axis and the first side edge; and
   a second vertical taper axis located intermediate the vertical central axis and the second side edge, and
   wherein the shield thickness is horizontally tapered such that the shield thickness at each of the first side edge and the second side edge is less than the shield thickness at the first vertical taper axis and the second vertical taper axis and such that the shield thickness at the vertical central axis is less than the shield thickness at the first vertical taper axis and the second vertical taper axis.

5. The conical face shield of claim 4, wherein the shield thickness is vertically tapered such that the shield thickness at each of the first arcuate edge and the second arcuate edge is less than the shield thickness at a point intermediate the first arcuate edge and the second arcuate edge.

6. The conical face shield of claim 5, wherein the first arc segment of the first arcuate edge and the second arc segment of the second arcuate edge are circular arcs.

7. The conical face shield of claim 1, further comprising:
   a bend intermediate the first arcuate edge and the second arcuate edge.

8. A face shield for attachment to a sports helmet, the face shield comprising:
   a conically-shaped face shield surface portion, the conically-shaped face shield surface portion:
   (1) extending arcuately from a left linear side edge to a right linear side edge, and
   (2) extending between an upper arcuate edge and a lower arcuate edge, wherein:
      a) the left linear side edge extends from a left end of the upper arcuate edge to a left end of the lower arcuate edge,
      b) the right linear side edge extends from a right end of the upper arcuate edge to a right end of the lower arcuate edge,
      c) the upper arcuate edge includes an upper arc segment and the lower arcuate edge includes a lower arc segment,
      d) wherein the upper arc segment is part of a first ellipse and the lower arcuate edge is part of a second ellipse, and
      e) wherein the semi-minor axis of the first ellipse is less than the semi-minor axis of the second ellipse.

* * * * *